United States Patent
Choi et al.

(10) Patent No.: US 11,668,666 B2
(45) Date of Patent: Jun. 6, 2023

(54) METHOD FOR EARLY DETECTION OF CARBONIZATION DURING DRYING OF ORGANIC MATERIAL

(71) Applicant: LG Chem, Ltd., Seoul (KR)

(72) Inventors: Yong Joon Choi, Daejeon (KR); Won Chan Park, Daejon (KR); Kyung Hyun Song, Daejeon (KR)

(73) Assignee: LG Chem, Ltd.

( * ) Notice: Subject to any disclaimer, the term of this patent is extended or adjusted under 35 U.S.C. 154(b) by 986 days.

(21) Appl. No.: 16/462,061

(22) PCT Filed: Feb. 23, 2018

(86) PCT No.: PCT/KR2018/002270
§ 371 (c)(1),
(2) Date: May 17, 2019

(87) PCT Pub. No.: WO2018/236026
PCT Pub. Date: Dec. 27, 2018

(65) Prior Publication Data
US 2019/0331619 A1    Oct. 31, 2019

(30) Foreign Application Priority Data

Jun. 23, 2017 (KR) .......... 10-2017-0079445

(51) Int. Cl.
*G01N 25/48* (2006.01)
*F26B 3/02* (2006.01)
(Continued)

(52) U.S. Cl.
CPC ............. *G01N 25/482* (2013.01); *F26B 3/02* (2013.01); *F26B 23/02* (2013.01); *G01K 11/003* (2013.01)

(58) Field of Classification Search
CPC .......... F26B 3/02; F26B 23/02; G01N 25/482; G01N 33/0065; G01N 25/56; G01N 33/004; G01K 11/003; A62C 3/04; G08B 17/117

See application file for complete search history.

(56) References Cited

U.S. PATENT DOCUMENTS

| 4,159,306 A * | 6/1979 | Borst ............. C01B 32/336 |
| | | 202/136 |
| 4,547,549 A * | 10/1985 | Nakamura ........... C08J 3/005 |
| | | 525/197 |

(Continued)

FOREIGN PATENT DOCUMENTS

| CN | 102634358 A | 8/2012 |
| DE | 202014101777 U1 | 6/2014 |

(Continued)

OTHER PUBLICATIONS

International Search Report for PCT/KR2018/002270, dated May 31, 2018.

(Continued)

*Primary Examiner* — Jessica Yuen
(74) *Attorney, Agent, or Firm* — Lerner David LLP

(57) ABSTRACT

The present invention relates to a method for early detection of carbonization during the drying of an organic material. The method of the present invention measures temperature variation per unit time of exhaust gas containing water ($H_2O$), carbon monoxide (CO), or carbon dioxide ($CO_2$), which are to be generated by the pyrolysis of an organic material, and the concentration of carbon monoxide/carbon dioxide of the exhaust gas, so as to determine the occurrence of carbonization therethrough, thereby enabling early detection of carbonization within a dryer.

10 Claims, 2 Drawing Sheets

(51) Int. Cl.
  *F26B 23/02* (2006.01)
  *G01K 11/00* (2006.01)

(56) References Cited

U.S. PATENT DOCUMENTS

| | | |
|---|---|---|
| 5,691,703 A | 11/1997 | Roby et al. |
| 7,941,937 B2 | 5/2011 | Do |
| 7,969,296 B1 | 6/2011 | Stell |
| 2005/0200475 A1 | 9/2005 | Chen |
| 2008/0127507 A1 | 6/2008 | Bindelle et al. |
| 2011/0021862 A1 | 1/2011 | Iwabuchi |
| 2012/0287285 A1 | 11/2012 | Jensen et al. |
| 2014/0047732 A1 | 2/2014 | Benje et al. |
| 2014/0203942 A1 | 7/2014 | Warmack et al. |
| 2015/0105527 A1 | 4/2015 | Gartner et al. |
| 2017/0082573 A1 | 3/2017 | Vingerhoets et al. |

FOREIGN PATENT DOCUMENTS

| | | | |
|---|---|---|---|
| EP | 2752660 A1 | | 7/2014 |
| JP | 2000192051 A | | 7/2000 |
| JP | 2001107052 A | | 4/2001 |
| JP | 2006232944 A | * | 9/2006 |
| JP | 2008524551 A | | 7/2008 |
| JP | 2008225857 A | | 9/2008 |
| JP | 2010155881 A | | 7/2010 |
| JP | 2014514523 A | | 6/2014 |
| JP | 5535730 B2 | | 7/2014 |
| JP | 5537666 B2 | | 7/2014 |
| JP | 2015504956 A | | 2/2015 |
| JP | 2015146285 A | | 8/2015 |
| JP | 2016117809 A | | 6/2016 |
| KR | 20040046226 A | | 6/2004 |
| KR | 20070038100 A | * | 4/2007 |
| KR | 20110083012 A | | 7/2011 |
| KR | 101135272 B1 | | 4/2012 |
| KR | 101284033 B1 | | 7/2013 |
| KR | 101365429 B1 | | 2/2014 |
| KR | 20150115279 A | | 10/2015 |
| KR | 20160133831 A | | 11/2016 |

OTHER PUBLICATIONS

Chinese Search Report for Application No. 201880004070.0 dated Mar. 18, 2021, pp. 1-3.
Forest Products Industry Handbook Writing Group "Forest Products Industry Handbook", Agricultural Press, Feb. 1978, pp. 747-749. (Providing English Translation of Abstract only).
Hao, Huatao et al., "Modern Wood Drying Technology", Northeast Forestry University Press, Jun. 2006, pp. 213-214. (Providing English Translation of Abstract only).
Extended European Search Report with Opinion for Application No. 18820234.5 dated Jan. 24, 2020.

* cited by examiner

[Fig. 1]
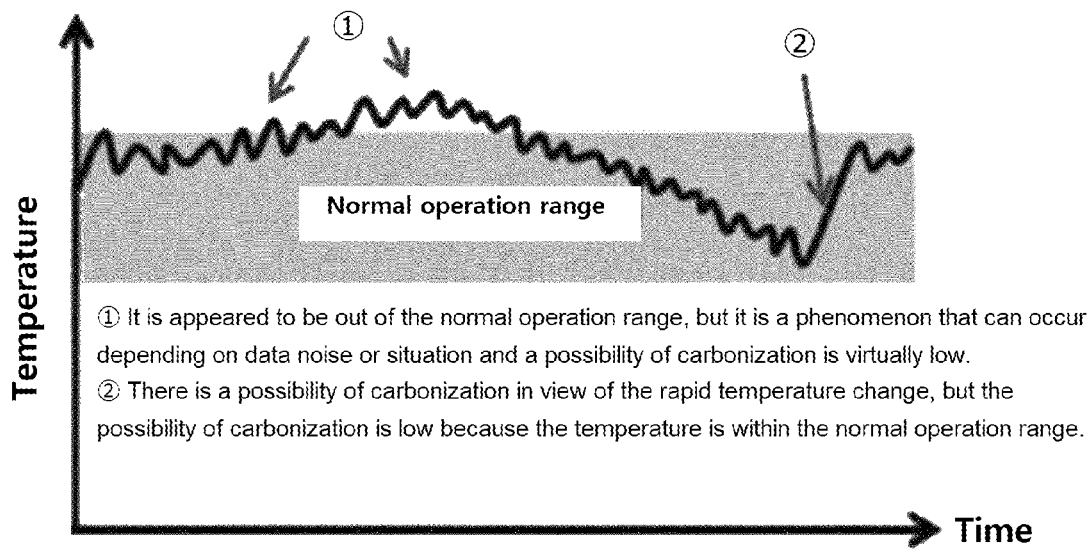
[Fig. 2]
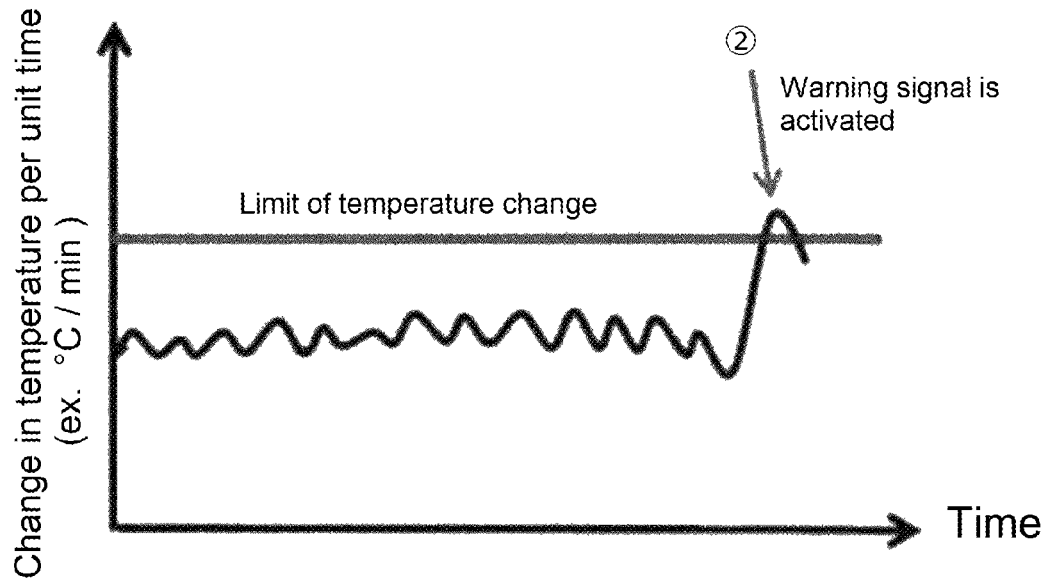

[Fig. 3]
1) Weak discoloration
2) Severe discoloration (Visible on the surface)
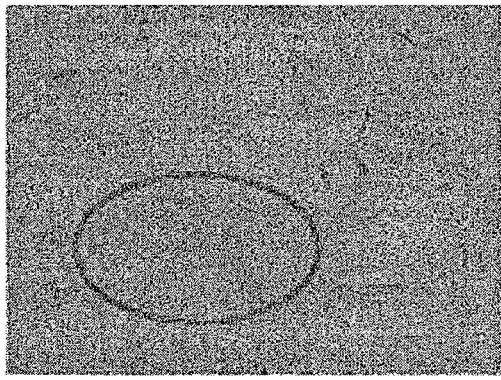
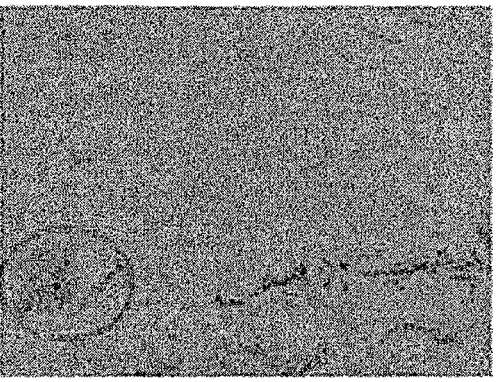
3) Carbonization progress
(Internal carbonization can be visually confirmed)
4) Carbonization / Smoke generated
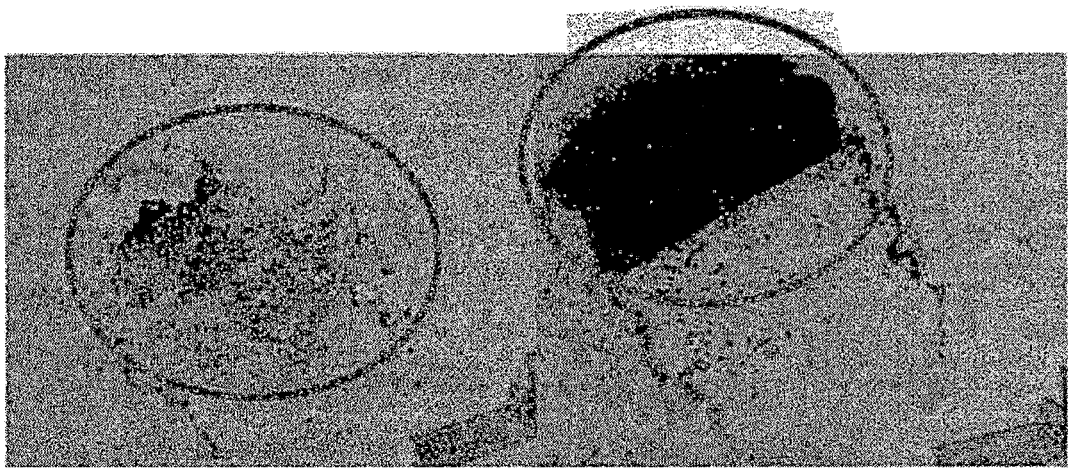

METHOD FOR EARLY DETECTION OF CARBONIZATION DURING DRYING OF ORGANIC MATERIAL

CROSS-REFERENCE TO RELATED APPLICATIONS

This application is a national phase entry under 35 U.S.C. § 371 of International Application No. PCT/KR2018/002270, filed Feb. 23, 2018, which claims priority to Korean Patent Application No. 10-2017-0079445, filed Jun. 23, 2017, the disclosures of which are incorporated herein by reference.

BACKGROUND OF THE INVENTION

1. Field of the Invention

The present invention relates to a method for the early detection of carbonization phenomenon to prevent safety accidents such as fire due to carbonization during a drying process of products made from organic materials in a dryer after synthesis of the products.

2. Description of the Related Art

Currently manufactured organic products, such as products of particle-based basic material are dried in a dryer through processes such as synthesis and dehydration and are allowed to meet specifications by controlling a temperature and a wind speed of hot air used in a drying process.

In general, among the various controllable drying factors, higher temperature of hot air is advantageous in terms of product quality (in terms of reduced residual solvent) and productivity. However, for product quality and safety, the product is dried with hot air below a certain level of temperature. Nevertheless, accidents caused by carbonization in the dryer have been continuously reported. Potential for carbonization is likely to lead to a major fire accident and therefore safety and productivity problems may occur.

The causes of most of carbonization phenomenon are not clear, so that prevention through the early detection of carbonization could be the best solution. Currently, it is common to check a temperature of exhaust emitted from the dryer or for an operator to directly smell and detect occurrence time of carbonization. However, this method is inaccurate in identifying the occurrence time of carbonization and may lead to safety accidents. Accordingly, a method for more accurately identifying the occurrence time of carbonization has been continuously required. It has found by the present inventors that a method for the early detection of carbonization phenomenon by using an increase in exhaust temperature, an increase in concentration of carbon monoxide/carbon dioxide in exhaust, and the like.

SUMMARY OF THE INVENTION

An object of the present invention is to provide a method for the early detection of carbonization phenomenon to prevent safety accidents such as fire due to carbonization during a drying process of products made from organic materials in a dryer after synthesis of the products.

In order to achieve the above object, the present invention provides a method for detecting exhaust temperature and concentration of carbon monoxide/carbon dioxide in exhaust for the prevention of safety accidents caused by unexplained causes inside a dryer using hot air and hot water.

The products made from organic materials are dried with hot air in a dryer after synthesis, dehydration, etc. When the organic materials are heated, water ($H_2O$), carbon monoxide (CO), carbon dioxide ($CO_2$) and the like are released by pyrolysis. In this process, an exothermic reaction is accompanied and the temperature rises, which causes an increase in the exhaust temperature.

The present invention provides a method for the detection of carbonization at an early stage by measuring an increase in exhaust temperature and/or a concentration of carbon monoxide/carbon dioxide generated according to an exothermic reaction occurred during carbonization. In the present invention, the concentration of carbon monoxide/carbon dioxide in exhaust is measured through a laboratory test (Lab Test) under conditions similar to those of actual fields to analyze ability for the detection of carbonization and real applications are presented based on the ability. In the case that the organic materials are dried at a high temperature and substances that are likely to be carbonized are dried, according to the method of the present invention, it can be expected to improve safety and productivity due to prevention of carbonization and fire.

The detection method according to the present invention is applied to a situation where it is impossible to visually identify the internal state of the dryer due to a large number of fine particles, that is, a situation where there is no method for identifying carbonization other than scenting odor outside. Also, the method is applied when it is impossible to install a gas concentration meter inside the dryer because of high internal temperature of the dryer and the gas concentration should be measured through a gas which is cooled down to a certain temperature after exhaust in the cyclone and the like.

In one embodiment, the present invention provides a method for the early detection of carbonization during a drying process of an organic material, comprising:

(1) hot-air drying the organic material in a dryer; and
at least one step of
(2) detecting a change in temperature per unit time of exhaust including water ($H_2O$), carbon monoxide (CO) or carbon dioxide ($CO_2$) emitted by the drying; or
(3) detecting a concentration of carbon monoxide in the exhaust; or
(4) detecting a concentration of carbon dioxide in the exhaust,
wherein it is determined that carbonization is occurred when the exhaust temperature rises at a rate of 0.5° C./min or more in the step (2), or when the concentration of carbon monoxide exceeds 2 ppm in the step (3), or when the concentration of carbon dioxide increases by 10% or more in the step (4).

In one embodiment, the organic material comprises polymer particles having a diameter of 500 μm or less.

In one embodiment, the area in which the drying and carbonization of the organic material occur is the inside of a large scale (having several tens of square meters) fluidized bed dryer (FBD: a dryer for drying the fluidized state of particles), which is mainly used in industry to dry polymer particles.

Effect of the Invention

According to the method for the early detection of carbonization of the present invention, it is possible to early detect carbonization in a dryer by determining the occurrence of carbonization through measurement of change in exhaust temperature of the dryer per unit time and/or the increase in the concentration of carbon monoxide/carbon dioxide in the exhaust.

BRIEF DESCRIPTION OF THE DRAWINGS

FIG. 1 illustrates a method for the detection of carbonization according to a comparative example, in which it is determined that carbonization is occurred when the internal temperature or the exhaust temperature of a dryer is out of a predetermined normal temperature range while monitoring the temperature during drying of products.

FIG. 2 illustrates a method for the detection of carbonization, in which a warning signal is activated when the increase of exhaust temperature is measured to be over predetermined value while monitoring a change in the exhaust temperature per unit time according to the present invention.

FIG. 3 illustrates the appearance change referenced in the "Results of laboratory test" table.

DETAILED DESCRIPTION OF THE INVENTION

Hereinafter, the present invention will be described in more detail.

The terms and words used in the present specification and claims should not be construed as limited to ordinary or dictionary meanings. They should be construed as meaning and concept consistent with the technical idea of the present invention based on the principle that the inventor can properly define the concept of the term in order to explain his invention in the best way.

In one embodiment, the method for the early detection of carbonization during a drying process of an organic material according to the present invention, comprises:

(1) hot-air drying the organic material in a dryer; and
at least one step of
(2) detecting a change in exhaust temperature per unit time including water ($H_2O$), carbon monoxide (CO) or carbon dioxide ($CO_2$) emitted by the drying; or
(3) detecting a concentration of carbon monoxide in the exhaust; or
(4) detecting a concentration of carbon dioxide in the exhaust, wherein it is determined that carbonization is occurred when the exhaust temperature rises at a rate of 0.5° C./min or more in the step (2), or when the concentration of carbon monoxide exceeds 2 ppm in the step (3), or when the concentration of carbon dioxide increases by 10% or more in the step (4).

In one embodiment, the method comprises two or more of the steps (2) to (4).

In one embodiment, the organic material comprises polymer particles having a diameter of 500 μm or less, for example at least one of acrylonitrile-butadiene-styrene (ABS), methyl methacrylate-butadiene-styrene (MBS), polyvinyl chloride (PVC) and high density polyethylene (HDPE).

In one embodiment, it is determined that carbonization is occurred when the change in temperature per unit time of exhaust including water ($H_2O$), carbon monoxide (CO) or carbon dioxide ($CO_2$) emitted by drying is 0.5° C./min or more. This can be changed depending on the materials and dryer conditions, for example, to 2° C./4 min.

In one embodiment, it is determined that carbonization is occurred when the concentration of carbon monoxide in the exhaust exceeds 2 ppm.

In one embodiment, it is determined that carbonization is occurred when the concentration of carbon dioxide in the exhaust increases by 10% or more.

In one embodiment, it is determined that carbonization is occurred when the change in temperature per unit time is 0.5° C./min or more and the concentration of carbon monoxide in the exhaust exceeds 2 ppm.

In one embodiment, it is determined that carbonization is occurred when the change in temperature per unit time is 0.5° C./min or more and the concentration of carbon dioxide in the exhaust increases by 10% or more.

In one embodiment, it is determined that carbonization is occurred when the concentration of carbon monoxide in the exhaust exceeds 2 ppm and the concentration of carbon dioxide in the exhaust increases by 10% or more.

In one embodiment, it is determined that carbonization is occurred when the change in temperature per unit time is 0.5° C./min or more, the concentration of carbon monoxide in the exhaust exceeds 2 ppm and the concentration of carbon dioxide in the exhaust increases by 10% or more.

As described above, the method for the early detection of carbonization according to the present invention enables to accurately identify the occurrence time of carbonization by using the specific criteria for generation of carbonization as compared with the conventional method. According to the present method, carbonization accident can be prevented, and stability and product productivity can be improved.

Hereinafter, the present invention will be described in more detail with reference to Examples. It will be apparent to those skilled in the art that the embodiments described below are intended to be illustrative of the present invention and are not intended to limit the scope of the present invention.

Comparative Example—Monitoring of Internal/Exhaust Temperature of Dryer

In this comparative example, the conventional method for the detection of carbonization will be described.

During drying products made from organic materials after synthesizing them, the internal or exhaust temperature of the dryer is monitored. If the temperature is out of the predetermined normal operation range, it is determined that there is a possibility of carbonization.

In the case of a large scale dryer, there is a lot of noise in measurement data of the internal temperature. Therefore, even if the actual carbonization does not occur, the temperature may be higher than a certain temperature or may be maintained over a certain temperature for a while, depending on the situation. In addition, there is a disadvantage that even if a rapid temperature change occurs due to carbonization, it is difficult to estimate the exothermic reaction due to carbonization when the temperature is within the normal operation range.

In this regard, referring to FIG. 1 showing the change of internal temperature of the dryer over time, in the case of "①", it is appeared to be out of the normal operation range, but it is a phenomenon that can occur depending on data noise or situation and a possibility of carbonization is substantially low. On the other hand, in the case of "②", there is a possibility to determine carbonization to be occurred in view of the rapid temperature change, but a real possibility of carbonization is low because the temperature is within the normal operation range.

Therefore, the conventional method for the detection of carbonization is not reliable in detecting accurate time point of carbonization.

Example

In the present example, the method for the detection of carbonization according to the present invention will be described.

1. Monitoring of Change in Exhaust Temperature of Dryer

In order to solve the problems of the comparative example, the change of the exhaust temperature per unit time can be analyzed and utilized.

The change of the exhaust temperature per unit time is monitored and it can be utilized as a method for checking carbonization by activating a warning signal when the temperature rise is measured to be above a certain value even though there is no special temperature change (If carbonization accompanied by an exothermic reaction occurs, a sudden temperature rise occurs).

In this regard, referring to FIG. 2 showing the change of exhaust temperature per unit time, there is a possibility of carbonization if the temperature rise exceeds the limit of temperature change (corresponding to "②").

As a result of a laboratory test (Lab Test) on carbonization, it can be determined that carbonization is occurred when the change in temperature per unit time is 0.5° C./min or more.

In fact, the results of monitoring the change in exhaust temperature per unit time have been applied to mass production.

2. Monitoring of Concentration of Carbon Dioxide in the Exhaust

In the carbonization process of organic materials, water and carbon monoxide/carbon dioxide are generated. Since carbon dioxide among them is generated in the largest amount, monitoring of the concentration of carbon dioxide can be utilized as a method for checking carbonization by activating a warning signal when the concentration exceeds a certain level.

As a result of a laboratory test (Lab test) on carbonization, it was confirmed that the concentration of carbon dioxide increased by 10% or more when carbonization and smoke generation were occurred. It can be determined that carbonization is occurred based on this result.

3. Monitoring of Concentration of Carbon Monoxide in the Exhaust

In the carbonization process of organic materials, it is known that carbon monoxide is generated in a relatively small amount, compared to carbon dioxide, for example, at a level of 1/10 to 1/5 of the amount of carbon dioxide generated.

Carbon dioxide generally exists in the air at a level of 400 ppm. However, the reference concentration thereof may actually vary by more than 100 ppm depending on the situation and environment, which causes data fluctuation. On the other hand, carbon monoxide exists in the air at 0 to 2 ppm, so that the base line of the reference concentration is clear and there is little data fluctuation.

Therefore, it can be determined that carbonization proceeds when the concentration of carbon monoxide exceeds 2 ppm.

The descriptions and results of the laboratory test (Lab test) carried out in the present invention, which reproduces the carbonization at the actual field, are described below.

Description About Laboratory Test

A laboratory test is for ABS powders that are dried in a fluidized bed dryer (FBD), but also the test is expected to be applicable to various types of dryers for other organic materials.

Purpose of laboratory test
This is to identify the possibility of the detection of $CO/CO_2$ by installing a detection instrument for monitoring of carbonization of ABS powders.
Contents of laboratory test
Carbonization phenomenon of powders accumulated in a dryer is reproduced.
Changes in appearance of ABS powders and changes in CO and $CO_2$ concentration due to the increase of a surface temperature, are observed.
Specification of $CO/CO_2$ meter for laboratory test
CO meter: accuracy: 5 ppm, range: 0 to 1,000 ppm, reaction time: ~30 sec
$CO_2$ meter: accuracy: 40 ppm, range: 0 to 4,000 ppm, reaction time: ~30 sec

Results of Laboratory Test

| Temperature of hot plate (° C.) | Test 1 | | | Test 2 | | |
|---|---|---|---|---|---|---|
| | CO (ppm) | $CO_2$ (ppm) | Appearance change | CO (ppm) | $CO_2$ (ppm) | Appearance change |
| 20 | 0 | 380-420 | No special | 0 | 485-520 | No special |
| 90 | 1-2 | | | 1 | 475-540 | |
| 125 | 2-3 | | | 1 | 470-490 | |
| 150 | 4 | | Weak discoloration | 2 | 490-540 | Weak discoloration [1] |
| 160 | 7 | Malfunction | Severe discoloration | 3-4 | 490-530 | Severe discoloration [2] |
| 170 | — | | | 4-5 | 490-500 | |
| 180 | | | | 6-12 | 480-530 | |
| 190 | — | | | 13-23 | — | Carbonization progress [3] |
| 200 | — | | | 23-34 | 480-500 | Carbonization progress |
| 210 | 44 | 465 | Carbonization/ smoke generated | 65 | 550-560 | Carbonization/ smoke generated [4] |

*The average concentrations of CO and $CO_2$ in the atmosphere are at a level of 0~2 ppm and of 400 ppm, respectively, but may vary depending on the environment.

The appearance change in the above table, that is, states of 1) to 4) with respect to surface discoloration, are illustrated in FIG. 3 (the circled portion indicates a state of a bottom surface).

Conclusion on Laboratory test
The reproduction of accumulated ABS powders and carbonization phenomenon due to the increase of a surface temperature, the changes of appearance due to the increase of a surface temperature, and the changes of CO and $CO_2$ concentrations are observed.

Carbonization phenomenon can be reproduced.

Regarding the concentration of carbon monoxide, it is observed that a slight change in concentration is occurred as carbonization progresses. Before smoke is generated and complete carbonization is occurred, it is observed that the change in concentration is relatively rapid. After smoke is generated, a sharp change in concentration is observed. From the results of observation, the ability of detecting carbonization by a carbon monoxide sensor is identified. There is an advantage that the reference concentration thereof is almost 0 ppm.

Regarding the concentration of carbon dioxide, the experimental equipment is simple and the accuracy of the equipment is low. Therefore, it is difficult to implement the measurement via a laboratory test. However, when carbonization is occurred and smoke is generated, it is observed that the concentration of carbon dioxide increases by about 10% compared to the reference concentration thereof (which can vary depending on the environment/situation). From the results of observation, the possibility of detecting carbonization by a carbon dioxide sensor is identified.

This experiment was carried out in an open space. However, it is considered that carbonization can be monitored by measuring the concentration in a dryer to be detected in a closed space, using a carbon monoxide/carbon dioxide meter with excellent performance.

While the present invention has been particularly shown and described with reference to figures and embodiments thereof, it will be understood by those of ordinary skill in the art that the scope of the present invention is not limited thereby and that various changes and modifications may be made therein. Therefore, the actual scope of the present invention will be defined by the appended claims and their equivalents.

What is claimed is:

1. A method for the early detection of carbonization during a drying process of an organic material, comprising:
   (1) hot-air drying the organic material in a dryer, wherein the hot-air drying produces an exhaust comprising one or more of water ($H_2O$), carbon monoxide (CO), and carbon dioxide ($CO_2$); and
   at least one of:
   (2) detecting a change in temperature per unit time of the exhaust; or
   (3) detecting a concentration of carbon monoxide in the exhaust; or
   (4) detecting a concentration of carbon dioxide in the exhaust,
   determining that carbonization has occurred when the change in temperature per unit time of the exhaust is 0.5° C./min or more.

2. The method for the early detection of carbonization according to claim 1, wherein the organic material comprises a polymer particle having a diameter of 500 μm or less.

3. The method for the early detection of carbonization according to claim 2, wherein the polymer particle is at least one of acrylonitrile-butadiene-styrene (ABS), methyl methacrylate-butadiene-styrene (MBS), polyvinyl chloride (PVC) and high density polyethylene (HDPE).

4. The method for the early detection of carbonization according to claim 1, wherein the dryer is a fluidized bed dryer.

5. The method for the early detection of carbonization according to claim 1, wherein the method comprises at least two of:
   (2) the detecting the change in temperature per unit time of the exhaust; or
   (3) the detecting the concentration of carbon monoxide in the exhaust; or
   (4) the detecting the concentration of carbon dioxide in the exhaust.

6. The method for the early detection of carbonization according to claim 1, further comprising determining that carbonization has occurred when the change in temperature per unit time of the exhaust is 0.5° C./min or more and the concentration of carbon monoxide in the exhaust exceeds 2 ppm.

7. The method for the early detection of carbonization according to claim 1, further comprising determining that carbonization has occurred when the change in temperature per unit time of the exhaust is 0.5° C./min or more and the change in concentration of carbon dioxide is 10% or more.

8. The method for the early detection of carbonization according to claim 1, further comprising determining that carbonization has occurred when the change in temperature per unit time of the exhaust is 0.5° C./min or more, the concentration of carbon monoxide in the exhaust exceeds 2 ppm and the concentration of carbon dioxide in the exhaust increases by 10% or more.

9. The method of claim 1, further comprising activating a warning signal after determining that carbonization has occurred.

10. A method for the early detection of carbonization during a drying process of an organic material, comprising:
    (1) hot-air drying the organic material in a dryer, wherein the hot-air drying produces an exhaust comprising one or more of water ($H_2O$), carbon monoxide (CO), and carbon dioxide ($CO_2$); and
    at least one of:
    (2) detecting a change in temperature per unit time of the exhaust; or
    (3) detecting a concentration of carbon monoxide in the exhaust; or
    (4) detecting a concentration of carbon dioxide in the exhaust,
    determining that carbonization has occurred when the concentration of carbon monoxide exceeds 2 ppm and when a change in the concentration of carbon dioxide is 10% or more.

* * * * *